(12) United States Patent
Huitema et al.

(10) Patent No.: US 6,626,849 B2
(45) Date of Patent: Sep. 30, 2003

(54) MRI COMPATIBLE SURGICAL BIOPSY DEVICE

(75) Inventors: Thomas W. Huitema, Cincinnati, OH (US); Jessica M. Pyzoha, Cincinnati, OH (US); James W. Vander Wende, Woodstock, VT (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/021,680

(22) Filed: Dec. 12, 2001

(65) Prior Publication Data

US 2003/0109803 A1 Jun. 12, 2003

Related U.S. Application Data

(60) Provisional application No. 60/334,765, filed on Nov. 1, 2001.

(51) Int. Cl.[7] .............................................. A61B 10/00
(52) U.S. Cl. ...................... 600/564; 600/567; 606/170
(58) Field of Search .............................. 600/562, 564, 600/565, 566, 567, 410, 411, 417, 420; 606/167, 170; 604/164.01, 164.11

(56) References Cited

U.S. PATENT DOCUMENTS

| 4,784,134 A | 11/1988 | Arana |
| 4,798,212 A | 1/1989 | Arana |
| 5,098,383 A | 3/1992 | Hemmy et al. |
| 5,534,778 A | 7/1996 | Loos et al. |
| 5,569,266 A | 10/1996 | Siczek |
| 5,855,554 A | 1/1999 | Schneider et al. |
| 6,007,497 A * | 12/1999 | Huitema ...................... 600/567 |
| 6,086,544 A | 7/2000 | Hibner et al. |
| 6,273,862 B1 * | 8/2001 | Privitera et al. ............ 600/568 |

FOREIGN PATENT DOCUMENTS

| EP | 640 842 A1 | 1/1995 | |
| GB | 2304580 A * | 3/1997 | ........... A61L/31/00 |
| WO | 96/08199 A1 | 3/1996 | |

OTHER PUBLICATIONS

The MRI–Compatible Mammotome—RSNA Nov. 1999, vol. 213 p. 454 (#1521).

* cited by examiner

Primary Examiner—Charles A. Marmor, II
(74) Attorney, Agent, or Firm—Dean Garner

(57) ABSTRACT

A biopsy device which is compatible for use with a magnetic resonance imaging machine. The device includes a non-metallic elongated substantially tubular needle having a distal end for insertion within tissue, a proximal end, and a longitudinal axis therebetween. The needle includes right and left members on either side of the longitudinal axis, where the right and left members each have upper and lower ends including a series of alternating male and female portions. The male portions of the right member mate with the female portions of the left member, and the male portions of the left member mate with the female portions of the right member to securely attach the two members together. The device further includes a port on the elongated needle for receiving a tissue sample.

20 Claims, 5 Drawing Sheets

MRI COMPATIBLE SURGICAL BIOPSY DEVICE

This application claims the benefit of U.S. Provisional Application Ser. No. 60/334,765, filed Nov. 1, 2001.

FIELD OF THE INVENTION

The present invention relates, in general, to devices for tissue sampling and, more particularly, to improved biopsy probes for acquiring subcutaneous biopsies and for removing lesions.

BACKGROUND OF THE INVENTION

The diagnosis and treatment of patients with cancerous tumors, pre-malignant conditions, and other disorders has long been an area of intense investigation. Non-invasive methods for examining tissue are palpation, Thermography, PET, SPECT, Nuclear imaging, X-ray, MRI, CT, and ultrasound imaging. When the physician suspects that tissue may contain cancerous cells, a biopsy may be done either in an open procedure or percutaneous procedure. For an open procedure, a scalpel is used by the surgeon to create a large incision in the tissue in order to provide direct viewing and access to the tissue mass of interest. Removal of the entire mass (excisional biopsy) or a part of the mass (incisional biopsy) is done. For a percutaneous biopsy, a needle-like instrument is used through a very small incision to access the tissue mass of interest and to obtain a tissue sample for later examination and analysis. The advantages of the percutaneous method as compared to the open method are significant: less recovery time for the patient, less pain, less surgical time, lower cost, less risk of injury to adjacent bodily tissues such as nerves, and less disfigurement of the patient's anatomy. Use of the percutaneous method in combination with artificial imaging devices such as X-ray and ultrasound has resulted in highly reliable diagnoses and treatments.

Generally there are two ways to percutaneously obtain a portion of tissue from within the body, by aspiration or by core sampling. Aspiration of the tissue through a fine needle requires the tissue to be fragmented into small enough pieces to be withdrawn in a fluid medium. The method is less intrusive than other known sampling techniques, but one can only examine cells in the liquid (cytology) and not the cells and the structure (pathology). In core sampling, a core or fragment of tissue is obtained for histologic examination, genetic tests, which may be done via a frozen or paraffin section. The type of biopsy used depends mainly on various factors present in the patient, and no single procedure is ideal for all cases. However, core biopsies seem to be more widely used by physicians.

Recently, core biopsy devices have been combined with imaging technology to better target the lesion. A number of these devices have been commercialized. One such commercially available product is marketed under the trademark name MAMMOTOME™, Ethicon Endo-Surgery, Inc. An embodiment of such a device is described in U.S. Pat. No. 5,526,822 issued to Burbank, et al., on Jun. 18, 1996, and is hereby incorporated herein by reference.

As seen from that reference, the instrument is a type of image-guided, percutaneous, coring, breast biopsy instrument. It is vacuum-assisted, and some of the steps for retrieving the tissue samples have been automated. The physician uses this device to capture "actively" (using the vacuum) the tissue prior to severing it from the body. This allows for sampling tissues of varying hardness. The device can also be used to collect multiple samples in numerous positions about its longitudinal axis without removing the device from the body. These features allow for substantial sampling of large lesions and complete removal of small ones.

Co-pending application Ser. No. 08/825,899 filed on Apr. 2, 1997, which is hereby incorporated herein by reference, described other features and potential improvements to the device including a molded tissue cassette housing permitting the handling and viewing of multiple tissue samples without physical contact by the instrument operator. Another feature described therein is the interconnection of the housing to the piercing needle using a thumbwheel, to permit the needle to rotate relative to the housing, while preventing the vacuum tube from wrapping about the housing. During use, the thumbwheel is rotated so that the device rotates within the lesion, and samples can be taken at different points within the lesion.

In actual clinical use for breast biopsy the instrument (probe and driver assembly) is mounted to the three axis-positioning head of an x-ray imaging machine. The three axis-positioning head is located in the area between the x-ray source and the image plate. The x-ray machines are outfitted with a computerized system which requires two x-ray images of the breast be taken with the x-ray source at two different positions in order for the computer to calculate x, y and z axis location of the suspect abnormality. In order to take the stereo x-ray images the x-ray source must be conveniently movable. The x-ray source therefore is typically mounted to an arm which, at the end opposite the x-ray source, is pivotally mounted to the frame of the machine in the region of the image plate.

Recently, there has been a need for a hand held core sampling biopsy device. This need has been fulfilled by Ethicon-Endo-Surgery in U.S. Pat. 6,086,544 issued on Jul. 11, 2000, which is hereby incorporated herein by reference. The aforementioned patent discloses a hand held MAMMOTOME™ core sampling biopsy device. The operator may steer the tip of the handpiece on the MAMMOTOME™ biopsy device with great freedom towards the tissue mass of interest. The surgeon has tactile feedback while doing so and can thus ascertain to a significant, degree, the density and hardness of the tissue being encountered. In addition, a hand held MAMMOTOME™ biopsy device is desirable because the handpiece on the MAMMOTOME™ may be held approximately parallel to the chest wall of the patient for obtaining tissue portions closer to the chest wall than may be obtained when using an instrument that is mounted to an electromechanical arm.

Recently, there has been a desire to use the above described biopsy devices with MRI imaging devices instead of x-ray imaging devices. However, existing medical biopsy sampling devices use small, multi-lumen probes extensively fabricated mostly if not entirely from metal. The metallic nature of these probes has many drawbacks. Typically these metal probes are electrically conductive and often magnetically weak, which interferes with their use under MRI guidance. The electrically conductive and magnetically weak nature of metal probes often work to create field distortions, called artifacts, on the image. The image of the lesion will show the metal probe, and this is problematic because the image of the probe can obscure the image of the lesion. Therefore, there has been a desire to have a generally non-metallic biopsy probe of the type described above. However, elimination of the artifact created by the metal probe entirely is also problematic because physicians rely extensively on some type of artifact to notify them as to where the tip of the probe is relative to the lesion.

SUMMARY OF THE INVENTION

In accordance with the present invention there is provided a biopsy device, which is compatible for use with a magnetic resonance imaging machine. The device includes a non-metallic elongated substantially tubular needle having a distal end for insertion within tissue, a proximal end, and a longitudinal axis therebetween. The needle comprising right and left members on either side of the longitudinal axis, wherein the right and left members each have upper and lower ends comprising a series of alternating male and female portions. The male portions of the right member mate with the female portions of the left member, and the male portions of the left member mate with the female portions of the right member to securely attach the two members together. The device further includes a port on the elongated needle for receiving a tissue sample.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
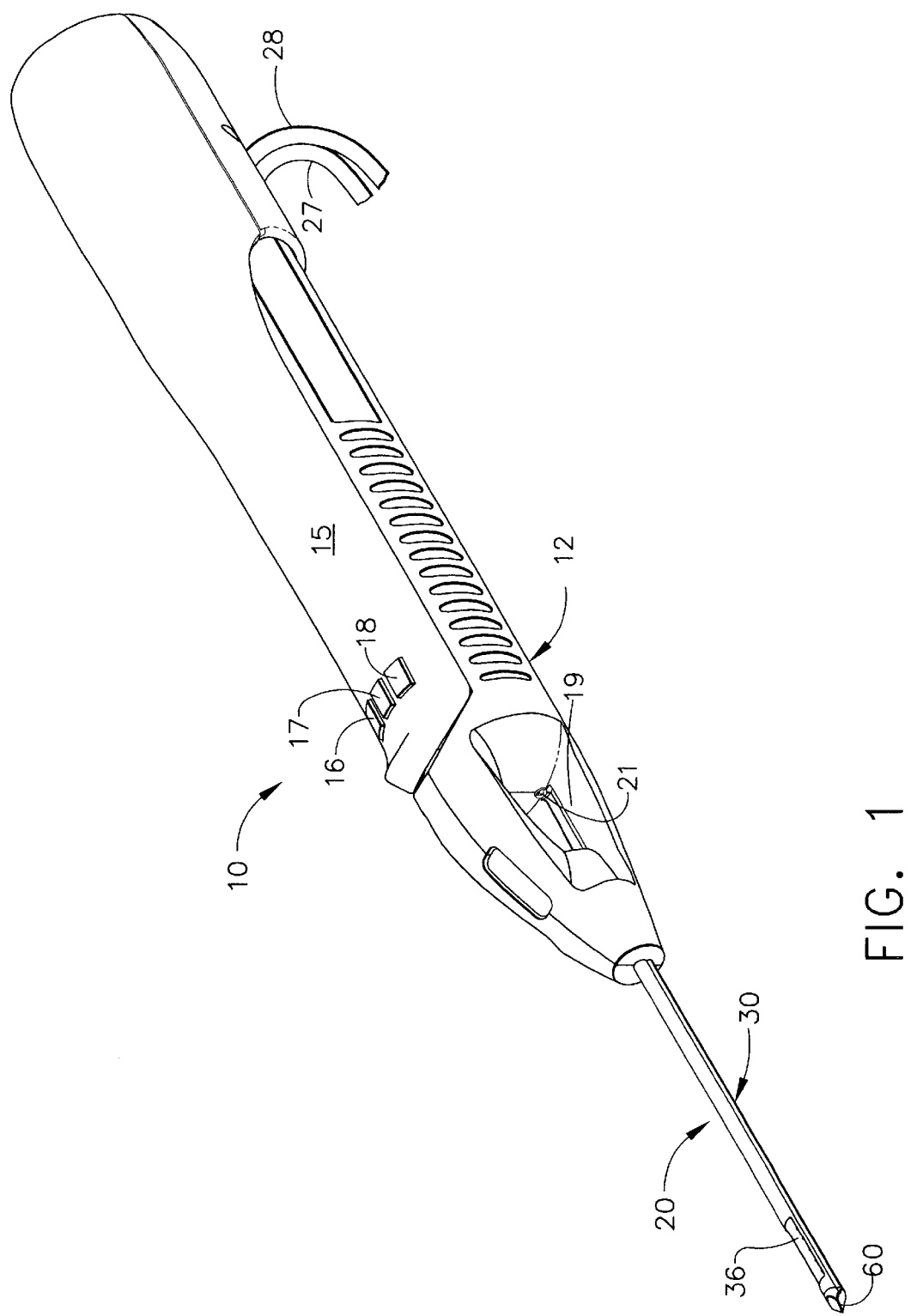
FIG. 1 is an isometric view of a hand held vacuum assisted biopsy device constructed in accordance with a preferred embodiment of this invention.

FIG. 1 shows a hand-held vacuum assisted biopsy device 10 comprising a needle assembly 20 and a holster 15. Needle assembly 20 is detachably connected to holster 15. Together they constitute a lightweight, ergonomically shaped, hand manipulatable portion referred to as handpiece 12. Since handpiece 12 is manipulated by the operator's hand rather than by an electromechanical arm, the operator may steer the handpiece 12 with great freedom towards the tissue mass of interest. The surgeon has tactile feedback while doing so and can thus, ascertain to a significant degree, the density and hardness of tissue being encountered. In addition, handpiece 12 may be held approximately parallel to the chest wall of a patient for obtaining tissue portions closer to the chest wall than may be obtained when using an instrument mounted to an electromechanical arm.

The device includes a means for obtaining a tissue sample. Holster 15 includes a forward button 16 which may be used to move cutter 21 (shown in FIG. 1) distally though cutter lumen 32 and sever tissue collected in port 36. Holster 15 further includes a reverse button 17 which may be used to move cutter 21 proximally through cutter lumen 32 and thereby moving the tissue sample in port 36 to a tissue collection surface 19. A vacuum button 18 on holster 15 is used to open or close first and second vacuum lines, 27 and 28, for activating a vacuum lumen 34 so as to cause tissue to become disposed within port 36.

Figure 2:
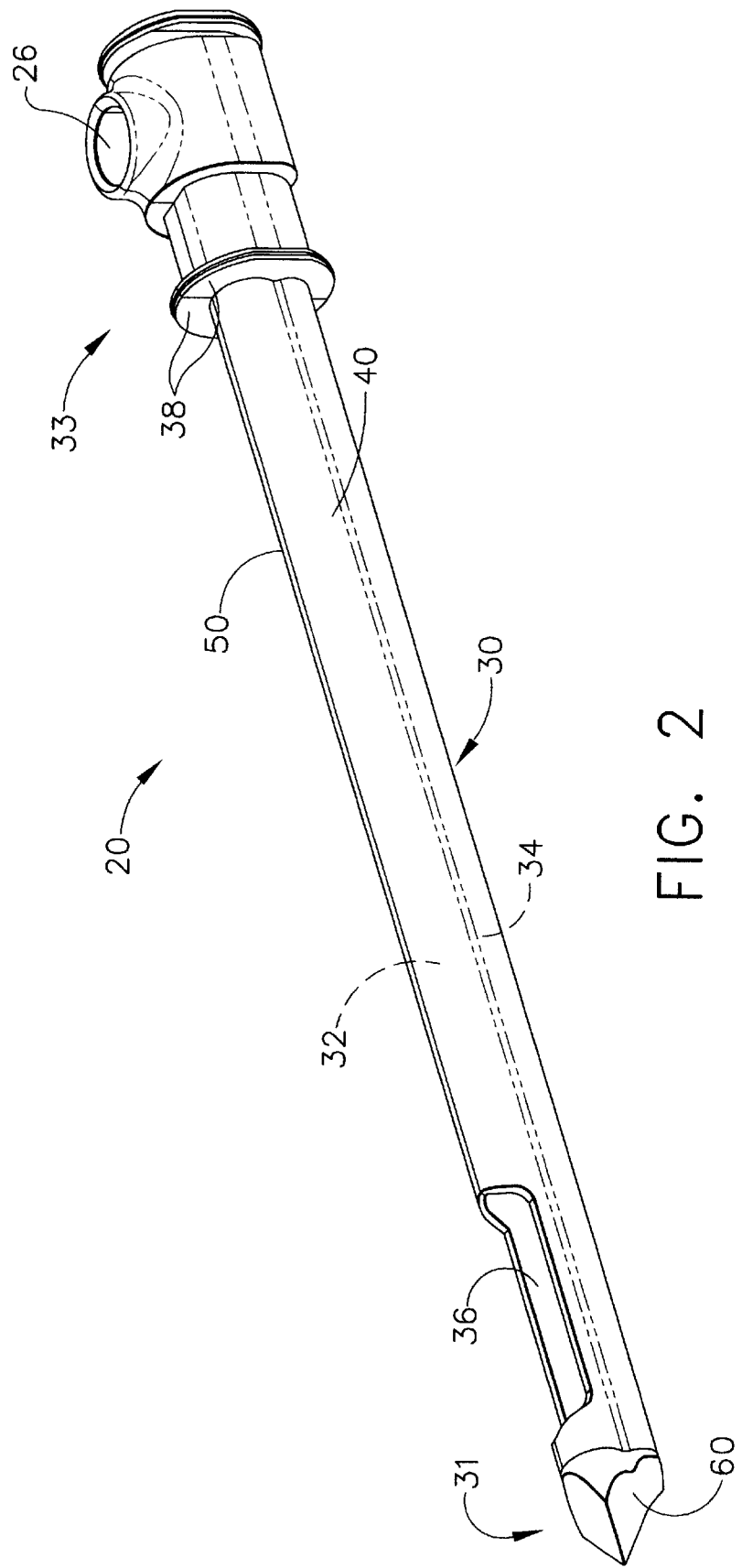
FIG. 2 is an isometric view of the elongated needle of the hand held vacuum assisted biopsy device of FIG. 1.

Referring now to FIG. 2 there is shown an isometric view of the needle assembly 20 of the hand held vacuum assisted biopsy device 10 of FIG. 1. Needle assembly 20 includes an elongated needle 30 having a distal end 31, a proximal end 33 and a longitudinal axis therebetween. Needle assembly 20 has a needle tip 60 at its distal end for penetrating the soft tissue of a surgical patient. Elongated needle 30 comprises a cutter lumen 32 and a vacuum chamber lumen 34.

At the distal end of the elongated needle 30 is a needle tip 60, which is sharpened and is preferably made from an MRI compatible resin such as ULTEM or VECTRA. Needle tip 60 is designed to penetrate soft tissue, such as the breast of a female surgical patient. In this embodiment, needle tip 60 is a three-sided pyramidal shaped point, although the needle tip 60 configuration may also have other shapes.

Figure 3:
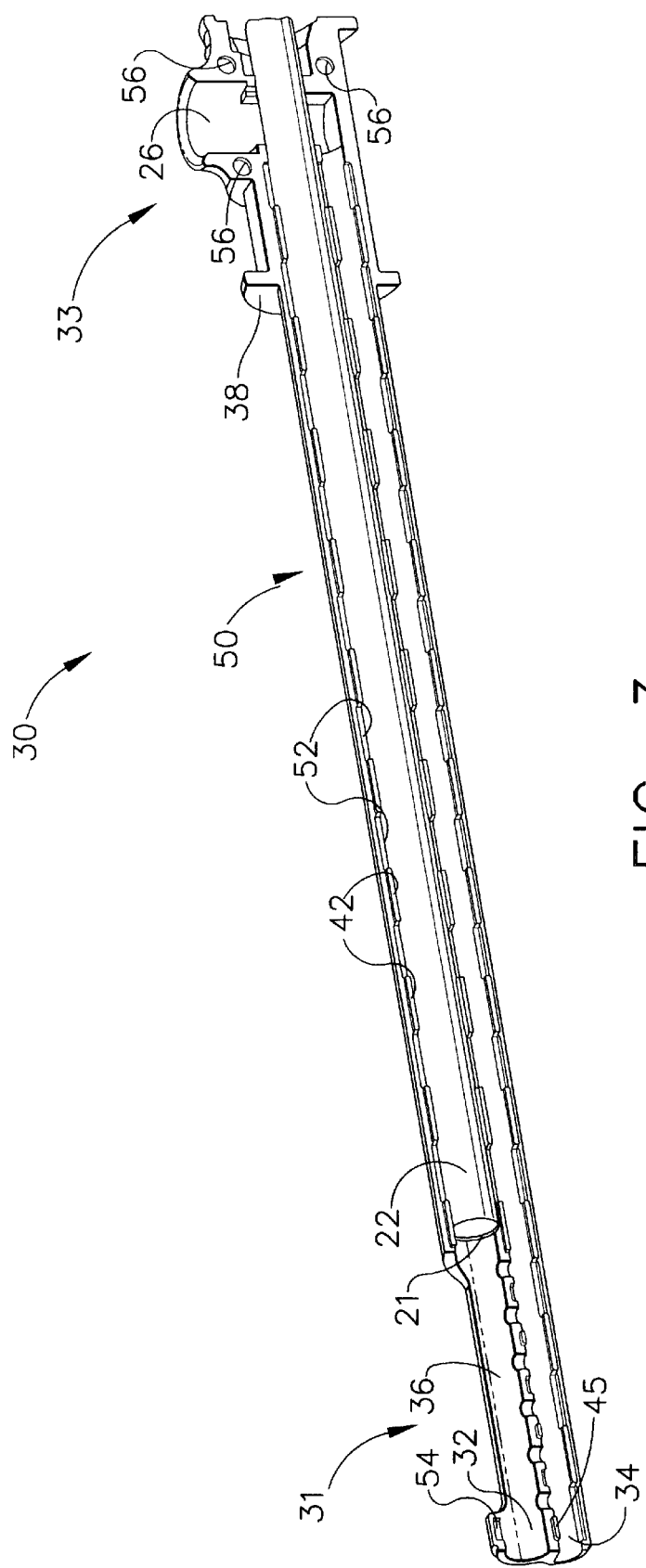
FIG. 3 is an isometric view of the right body member of the elongated needle of the hand held vacuum assisted biopsy device of FIG. 1. A cutter tube liner is illustrated in assembly with the elongated needle.

Referring now to FIG. 3, elongated needle 30 is preferably made from a thermoplastic material such as VECTRA A130 or B130 liquid crystal polymer, although other MRI compatible resins may be available from Ticona of Summit, N.J. Elongated needle 30 includes a cutter lumen 32 which houses the cutter 21 (shown in FIG. 1). Adjacent the distal end 31 of the cutter lumen 32 is a port 36 for receiving the tissue that is extracted from a surgical patient by the cutter 21. Joined alongside the cutter lumen 32 is a vacuum chamber lumen 34. The vacuum chamber lumen 34 receives vacuum from the second vacuum line 28 which is connected the vacuum chamber lumen 34 on the elongated needle 30 by the vacuum manifold 26 which is located at the proximal end 33 of elongated needle 30. Also located at the proximal end of the elongated needle 30 is a flange 38, which allows the elongated needle 30 and needle assembly 20 to interlock with the handpiece 12 on the hand-held vacuum assisted biopsy device 10. Changing from a stainless steel needle to a polymer may require a change in wall thickness, for example from 0.008" to 0.030". The liner 22, discussed below, is also made from a MRI compatible material, preferably a polypropylene such as PROLENE available from Ethicon, Inc., Somerville N.J., or a material known as RADEL 5000, available from British Petroleum, London UK.

Figure 4:
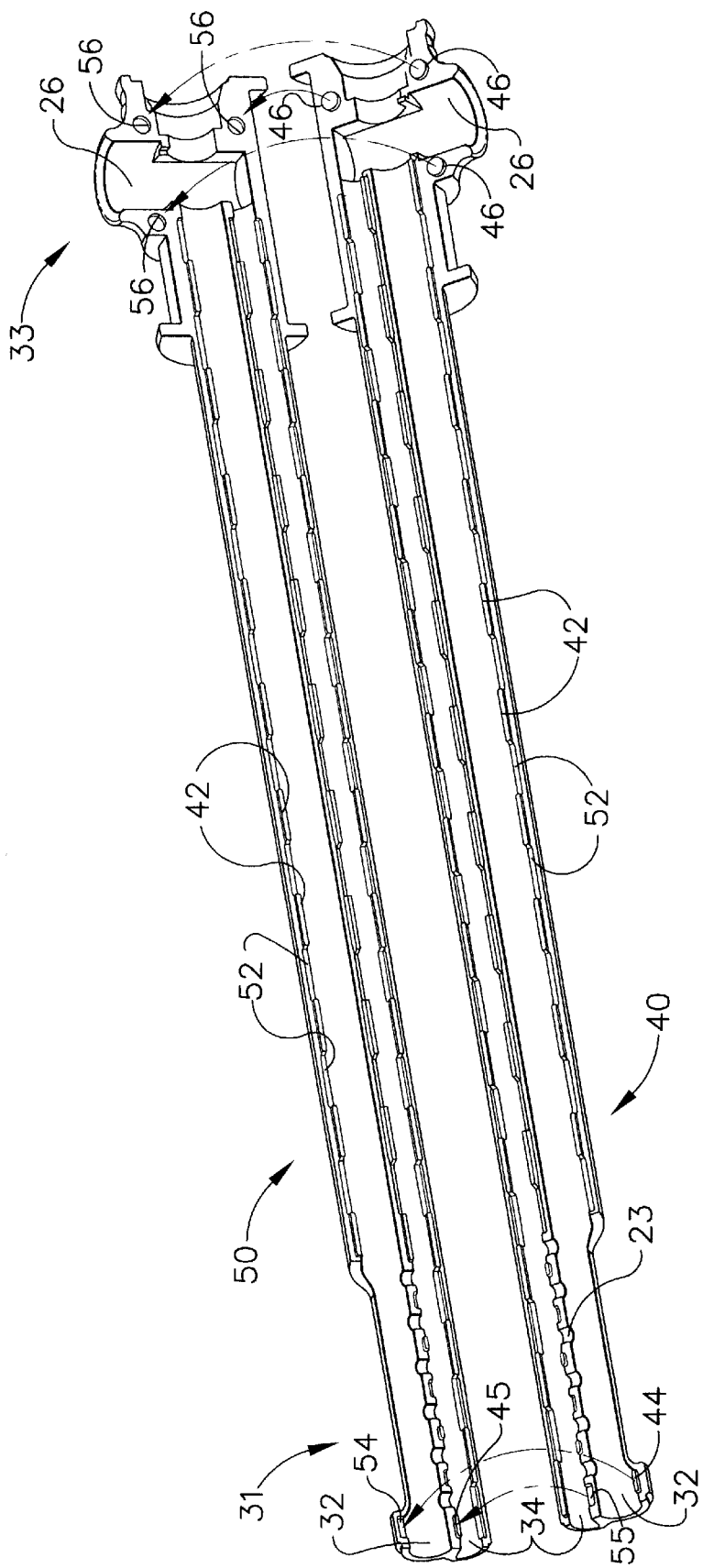
FIG. 4 is an exploded isometric view of the separated left body member and right body member of the elongated needle of the hand held vacuum assisted biopsy device of FIG. 1.

As seen in FIG. 4, elongated needle 30 is formed from a left body member 40 and a right body member 50 on either side of the longitudinal axis. The edges of the halves 40 and 50 are gated for easy part filling, and the edges are stepped with ridges that allow the two halves 40 and 50 to attach together with ease. Preferably needle 30 is molded from a very stiff thermoplastic, such as VECTRA A130 or VECTRA B130 liquid crystal polymer. Other glass fiber reinforced resins known to those skilled in the art could also be used. Preferably the probe is made from a polymer material having the combination of high stiffness, low viscosity, and low mold shrink rate, such as LCP resins.

During assembly of one potential embodiment the elongated needle 30, the left body member 40 and right body member 50 of the elongated needle 30 are pushed together. Once the left body member 40 and the right body member 50 are pressed together, a thin-walled sleeve of high strength tubing is slipped over the elongated needle and is shrink fitted into place. The shrink tubing holds the left body member 40 and the right body member 50 together for easier handling prior to adhesive curing. In addition, the shrink tubing makes the exterior of the elongated needle 30 smoother for reduced insertion forces.

Referring back to FIG. 3, there is shown the right body member 50 of the elongated needle 30, separated from the left body member 40, which has been omitted from this figure for clarity. The right body member 50 has upper and lower ends comprising alternating male and female portions or members, 42 and 52, which alternate and are arranged axially along the length of the right body member 50 of the elongated needle 30. In addition to the male and female members, 42 and 52, there is an upper female distal member 54 and a lower male distal member 45, both of which are located at the distal end of the right body member 50. The upper female distal member 54 is located just above the distal end of the cutter lumen 32 and above the distal end of the vacuum chamber lumen 34. At the proximal end of the right body member 50 are three female receivers 56 which surround the vacuum manifold 26 at the proximal end of the right body member 50.

Still referring to FIG. 3, needle assembly 20 includes a cutter tube liner 22, which helps keep adhesive out of the lumen to provide a smooth surface thereon. Liner 22 generally abuts the outer surface of cutter 21 along lumen 32. The distal end of liner 22 is proximal to port 36 but otherwise is disposed along the length of lumen 32. The cutter tube liner 22 is formed from a thin-walled extrusion of a low-friction, abrasion-resistant plastic, such as polypropylene, polyetherimide or polyethersulfone. The cutter tube liner 22 provides a smooth, low-friction, abrasion-resistant surface for the cutter 21. The cutter tube liner 22 also acts as an aid for sealing vacuum and fluid leakage in that it isolates the cutter lumen 32 from the vacuum chamber lumen 34 and ensures that fluid and material from the cutter lumen 32 does not get sucked into the vacuum chamber 34 by vacuum suction in the vacuum chamber lumen 34. Isolating the cutter lumen 32 from the vacuum chamber lumen 34 may be preferable because the cutter lumen 32 operates on the first vacuum line 27, and the vacuum chamber lumen 34 operates on the second vacuum line 28.

Still referring to FIG. 3, another feature that is included in the preferred design of the invention to enhance performance is the outside diameter of the left body member 40 and right body member 50 could be stepped very slightly, if needed, to compensate for the thickness of the cutter tube liner 22. This is, the cutter lumen 32 would be very slightly larger than the inside diameter of the cutter tube liner 22, which is a thin walled structure.

Referring again to FIG. 4 there is shown an exploded isometric view of the elongate needle 30 of the hand held vacuum assisted biopsy device 10 of FIG. 1. Both the left body member 40 and the right body member 50 of the elongated needle 30 are shown. The male features 42, which are arranged axially on the left body member 40, mate to the female features 52, which are arranged axially on the right body member 50. Also, the male features 42 which are arranged axially on the right body member 50 mate to the female features 52 which are arranged axially on the left body member 40.

In addition to male and female members, 42 and 52, which are arranged axially and mate, the left body half 40 and right body member 50 have additional features that mate at both the proximal and the distal ends. At the proximal end of the right body member 50 are three female receivers 56 which surround the vacuum manifold 26. At the proximal end of the left body member 40 are three male bosses 46 which surround the vacuum manifold 26 and correspond to the three female receivers 56 on the right body member 50. When the left body member 40 and the right body member 50 are pushed together, the three female receivers 56 on the proximal end of the right body member 50 receive the three corresponding male bosses 46 of the left body member 40. The proximal end of the elongated needle 30 is thus, retained by the three female receivers 56 and three male bosses 46, which mate at the proximal end of the elongated needle 30.

The needle tip 60 at the distal end of the elongated needle 30 is retained by the upper female distal part 54 and the upper male distal portion 44 and the lower female distal part 55 and the lower male distal portion 45. On the left body member 40 is and upper male distal portion 44 and a lower female distal part 55. The upper male distal portion 44 is located above the cutter lumen 32 at the distal end on the left body member 40, and the lower female distal part 55 is located below the cutter lumen 32 and above the vacuum chamber lumen 34 at the distal end of the left body member 40. On the right body 50 is an upper female distal part 54 and a lower male distal portion 45, which correspond to the upper male distal portion 44 and the lower female distal part 55 on the left body member 40. The upper female distal part 54 is located above the cutter lumen 32 at the distal end of the right body member 50, and the lower male distal portion 45 is located below the cutter lumen 32 and above the vacuum chamber lumen 34 at the distal end of the right body member 50.

Still referring to FIG. 4, not only do the male and female members, 42 and 52, secure the body of the elongated needle 30, and the proximal and distal ends of the elongated needle 30, both male and female members, 42 and 52, also form the interlumen vacuum holes 23, which are located below the port 36 on the distal end of the elongated needle 30. The male and female members 42 and 52, on the right body member 50, which are located below the port 36 in between the cutter lumen 32 and vacuum chamber lumen 34, mate with male and female members, 42 and 52, on the left body member 40, which are also located below the port 36 in between the cutter lumen 32 and vacuum chamber lumen 34. When these male and female members, 42 and 52, on the left body member 40 and right body member 50 mate, the interlumen vacuum holes 23 on the needle 30 are formed. The interlumen vacuum holes 23 are six cylindrically shaped holes which are open to port 36, so that the tissue can be severed by the cutter 21, which rotates and advances. The cutter 21 deposits the tissue into the tissue collection surface 19 by retracting proximally.

Still referring to FIG. 4, during assembly of the elongated needle 30, sufficient adhesive is applied to the left body member 40 and right body member 50, to fill the narrow axial spaces between the male and female members, 42 and 52, which mate. After this, the left body member 40 and right body member 50 are pressed together. The adhesive that is used should be cured using light, heat, or other appropriate means for the particular types of adhesive that is being used. For a light cured adhesive, light could be directed inside of the cutter lumen 32 and the vaccum lumen 34 using light stick optics if necessary.

Still referring to FIG. 4, the male and female members, 42 and 52, which mate and are located on the left body member 40 and the right body member 50 have a number of distinct advantages. The male and female members, 42 and 52, on the left body member 40 and right body member 50 orient the left body member 40 and right body member 50 during assembly of the elongated needle 30.

The male and female members, 42 and 52, which mate, are also key factors in increasing both the strength and lateral bending stiffness of the elongated needle 30. When the needle 30 is subjected to a lateral bending moment, nearly all of the material being loaded axially is the high-strength, high stiffness body material. Only the small amount of adhesive that is used to fill the axial clearances between the male and female members, 42 and 52, which mate, is of a lower stiffness. A conventional bonded joint would result in the bond line being loaded in a manner similar to that used for adhesive peel strength testing, which is the most severe type of loading for an adhesive joint. In contrast to this, the male and female members, 42 and 52, which mate, would create lateral bond surfaces along the elongated needle 30. This substantially increases the bond line length of the elongated needle 30. Because of significant portions of the bond line being loaded in shear, the strength and lateral stiffness of the elongated needle 30 is increased. This is improved over a single piece molded cylinder in that with the bond line loaded in shear, the elongated needle 30 will be able to sustain bending moments of its joints rather than at its base, which decreases the possibility of breakage.

Figure 5:
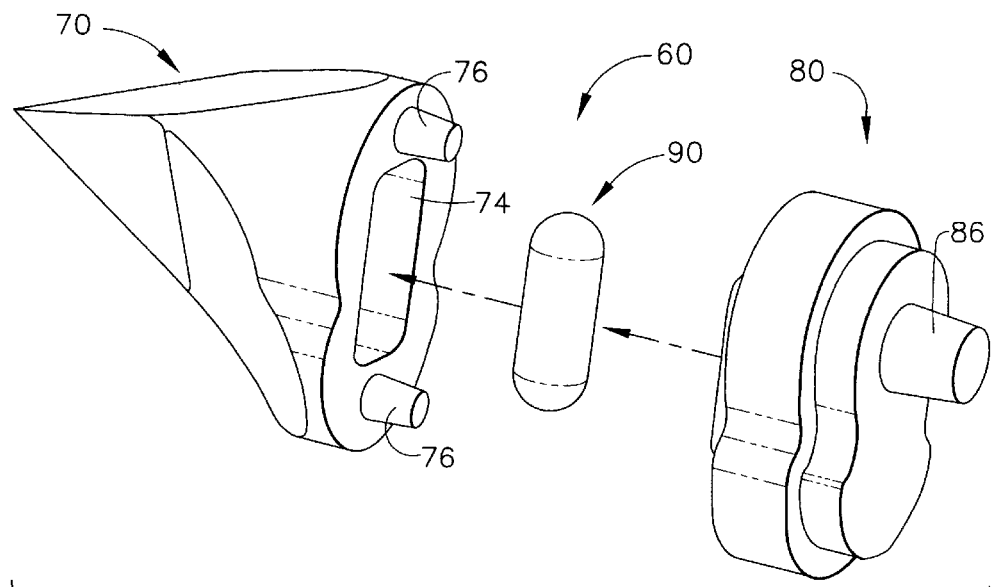
FIG. 5 is an exploded isometric view of the two member needle tip on the elongated needle of the hand held vacuum assisted biopsy device of FIG. 1 as viewed from the proximal side thereof.

FIG. 5 shows an exploded isometric view of the needle tip 60 of the elongated needle 30 of the hand held vacuum assisted biopsy device 10 of FIG. 1 as viewed from the proximal side thereof. The needle tip 60 has two halves; a composite tip member 70, and a composite hub member 80. Both the composite tip member 70 and the composite hub member 80 are preferably molded from a magnetic Resonance Imaging (MRI) compatible resin such as ULTEM or VECTRA ceramic or other MRI compatible materials known to those skilled in the art. The composite tip member 70 has a three-sided pyramidal shaped point, but may also have other shapes. The composite tip member 70 has a hollow cavity 74 and protruding connectors 76. The two protruding connectors 76 are inserted into the two receiving holes 82 on the composite hub member 80 when the composite hub member 80 is pushed into the composite tip member 70 during assembly. The cavity preferably contains a capsule 90 made from a material which will leave an MRI artifact. Having a capsule 90 made from an MRI artifact leaving material is necessary because since the elongated needle 30 is made of an MRI compatible resin, the elongated needle 30 does not show up on an MRI scan. Therefore, it is difficult for a physician to discern the orientation of the elongated needle 30 during an MRI scan, MRI artifact leaving material 90 solves the aforementioned problems in that a needle tip 60 leaves a small, but not troublesome artifact on an MRI scan. This small, artifact indicates the orientation of the elongated needle 30 relative to the sight of biopsy, and where the tissue receiving bowl begins during an MRI scan. The MRI artifact leaving material 90 that is preferred is a capsule of Gadolinium. However, there are other materials that could be put into the hollow cavity 74 of the composite tip member 70 that would leave an acceptable MRI artifact. These include, but are not limited to: liquid Gadolinium, Titanium Wire, Aluminum, Copper, Brass Iron, and Bronze.

Figure 6:
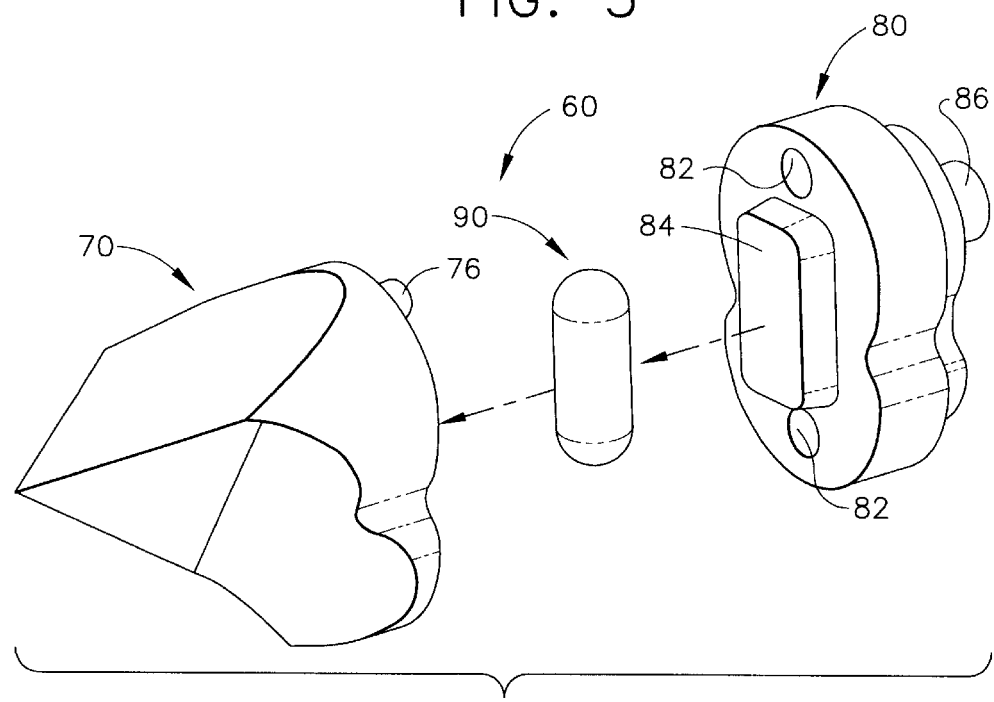
FIG. 6 is an exploded isometric view of the two member needle tip of the elongated needle of the hand held vacuum assisted biopsy device of FIG. 1 as viewed from the distal end thereof.

FIG. 6 shows an exploded isometric view of the needle tip 60 of the elongated needle 30 of the hand held vacuum assisted biopsy device 10 of FIG. 1 as viewed from the distal end thereof. This figure clearly illustrates the components on the composite hub member 80. On the distal end of the composite hub member 80 is a male part 84, which pushes the MRI artifact leaving material 90 down into the hollow cavity 74 on the composite tip member 70. Also located on the distal end of the composite hub member 80 is a knock out boss 86, which pushes a collected breast tissue sample into the end of the cutter tube 21 of the hand held vacuum assisted biopsy device 10 during a breast biopsy. The two receiving holes 82 on the composite hub member 80 receive the two protruding connectors 76 on the composite tip member 70 when the composite tip member 70 and composite hub member 80 are pushed together. The reception of the two protruding connectors 76 on the composite tip member 70 by the two receiving holes 82 on the composite hub member 80 locks the composite tip member 70 and the composite hub member 80 together, and seals the MRI artifact leaving material 90 in the hollow cavity 74 in between the composite tip member 70 and composite hub member 80.

In using the hand held vacuum assisted biopsy device 10, as shown in FIG. 1, for a breast biopsy in an MRI environment, the physician will be positioned outside of the MRI magnet, the patient is moved into the MRI magnet and imaging of the breast is performed. During imaging of the breast, serial slices of the breast are examined, and a contrast agent is administered to highlight suspicious areas of breast tissue. At this time, the location of the suspicious breast tissue is determined relative to the compression grid.

After the location of the suspicious breast tissue is determined, the patient is moved outside the magnet. Local anesthesia is administered to the patient and a probe is inserted into the area of suspicious breast tissue.

After the probe is inserted into the suspicious area of breast tissue, the patient is moved back into the MRI magnet and a set of images of the breast are taken. The sets of images confirm that the probe is adjacent to the suspicious breast tissue, the patient is moved outside of the MRI magnet, and the hand held vacuum assisted biopsy device 10 of FIG. 1 is then inserted into the sleeve, replacing an obturator.

After the hand held vacuum assisted biopsy device 10 of FIG. 1 is inserted through the sleeve; multiple tissue samples are taken. In taking multiple tissue samples, the needle tip 60 at the distal end of the elongated needle 30 on the hand held vacuum assisted biopsy 10, of FIG. 1, penetrates the breast in the area that is adjacent of the suspicious breast tissue. Prior to, and during penetration by the needle tip 60, the cutter 21 is fully forward, and is advanced forward through the cutter lumen 32 by pressing the forward button 16 on the holster 15 of the vacuum assisted biopsy device 10 of FIG. 1.

Once the elongated needle 30 is positioned in the area adjacent to the suspicious breast tissue, vacuum suction is applied to the vacuum chamber lumen 34. The vacuum suction is applied by pressing the vacuum button 18 on the holster 15 of the hand held vacuum assisted biopsy device 10 of FIG. 1. Pressing the vacuum button 18 on the holster 15 opens the second vacuum line 28, which transports vacuum suction through the handpiece 12 of the hand held vacuum assisted biopsy device 10 and into the vacuum chamber lumen 34 on the elongated needle 30. The second vacuum line 28 runs through the handpiece 12 of the hand held vacuum assisted biopsy device 10 and into the elongated needle 30 through the vacuum manifold 26 at the proximal end of the elongated needle 30. The vacuum suction that is applied to the vacuum chamber lumen travels from the proximal, and to the distal end of the vacuum chamber lumen 34, below the interlumen vacuum holes 23. The interlumen vacuum holes 23 receive suction from the vacuum chamber lumen 34.

After the cutter has been retracted, the suction from the interlumen vacuum holes 23 actively pulls breast tissue through the port 36 and into the cutter lumen 32 of the elongated needle 30. After the breast tissue is pulled into the elongated needle 30 through the port 36, the cutter 21 begins to rotate and advances through the breast tissue until a sample has been obtained. After the breast tissue sample has been obtained, the elongated needle 30 is rotated to position the port 36 toward a different clockwise position in preparation for obtaining the next tissue sample. After the elongated needle 30 is rotated, the cutter 21 is withdrawn backwards within the cutter lumen 32 of the elongated needle 30 and the breast tissue sample is carried to a knock-out boss 86, which pushed the collected breast tissue sample out into a tissue collection surface 19 on the handheld vacuum assisted biopsy device 10. Vacuum suction is then reapplied to the vacuum chamber lumen 34 from the second vacuum line 28, and the aforementioned process is repeated continuously until the elongated needle 30 has been rotated clockwise once 360°.

After multiple breast tissue samples have been obtained from the patient, the patient is moved back into the MRI magnet. Once in the MRI magnet, a set of images of the breast are taken in order to confirm that the suspicious breast tissue has been removed. The artifact in the probe tip is a useful point of reference to confirm after the biopsy site is marked, the breast biopsy in an MRI environment is complete.

While preferred embodiments of the present invention have been shown and described herein, it will be obvious to those skilled in the art that such embodiments are provided by way of example only. Numerous variations, changes, and substitutions will now occur to those skilled in the art without departing from the present invention. Accordingly, it is intended that the invention be limited only by the spirit and scope of the appended claims.

What is claimed is:

1. A biopsy device which is compatible for use with a magnetic resonance imaging machine, said device comprising:
    a. a non-metallic elongated substantially tubular needle having a distal end for insertion within tissue, a proximal end, and a longitudinal axis therebetween, said needle comprising right and left members on either side of said longitudinal axis, said right and left members each having upper and lower ends comprising a series of alternating male and female portions, wherein said male portions of said right member mate with said female portions of said left member and said male portions of said left member mate with said female portions of said right member to securely attach said two members together; and
    b. a port on said elongated needle for receiving a tissue sample.

2. The device of claim 1 wherein said needle comprises a thermoplastic.

3. The device of claim 1 wherein said needle comprises a glass fiber reinforced polymer resin.

4. The device of claim 1 further including a sleeve disposed over said needle.

5. The device of claim 4 wherein said sleeve comprises high strength shrink fitted tubing.

6. The device of claim 1 wherein adhesive is disposed on said upper and lower ends of said needle for attachment of said right and left members.

7. The device of claim 1 wherein said needle has a longitudinal lumen extending therein, and said lumen having a liner extending therethrough.

8. A biopsy device which is compatible for use with a magnetic resonance imaging machine, said device comprising:
    a. a handle and a non-metallic elongated substantially tubular needle having a proximal end attached to said handle, a sharp distal end for insertion within tissue, and a longitudinal axis therebetween;
    b. said needle comprising right and left members on either side of said longitudinal axis, said right and left members each having upper and lower ends comprising a series of alternating male and female portions, wherein said male portions of said right member mate with said female portions of said left member and said male portions of said left member mate with said female portions of said right member to securely attach said two members together; and
    c. a means for obtaining a tissue sample within said elongated needle.

9. The device of claim 8 wherein said needle comprises a thermoplastic.

10. The device of claim 8 wherein said needle comprises a glass fiber reinforced polymer resin.

11. The device of claim 8 further including a sleeve disposed over said needle.

12. The device of claim 11 wherein said sleeve comprises high strength shrink fitted tubing.

13. The device of claim 8 wherein adhesive is disposed on said upper and lower ends of said needle for attachment of said right and left members.

14. The device of claim 8 wherein said needle has a longitudinal lumen extending therein, and said lumen having a liner extending therethrough.

15. A biopsy device which is compatible for use with a magnetic resonance imaging machine, said device comprising:
    a. a handle and a non-metallic elongated substantially tubular needle having a proximal end attached to said handle, a sharp distal end for insertion within tissue, and a longitudinal axis therebetween comprising a lumen, said needle further including a port for receiving a tissue sample;
    b. said needle comprising right and left members on either side of said longitudinal axis, said right and left members each having upper and lower ends comprising a series of alternating male and female portions, wherein said male portions of said right member mate with said female portions of said left member and said male portions of said left member mate with said female portions of said right member to securely attach said two members together; and
    c. a cutter for obtaining a sample of tissue which is disposed within said port.

16. The device of claim 15 wherein said needle comprises a thermoplastic.

17. The device of claim 15 wherein said needle comprises a glass fiber reinforced polymer resin.

18. The device of claim 15 further including a sleeve disposed over said needle.

19. The device of claim 18 wherein said sleeve comprises high strength shrink fitted tubing.

20. The device of claim 15 wherein adhesive is disposed on said upper and lower ends of said needle for attachment of said right and left members.

* * * * *